(12) United States Patent
McCrary et al.

(10) Patent No.: US 7,635,361 B2
(45) Date of Patent: Dec. 22, 2009

(54) HIGHLY EFFICIENT FLUID SUCTIONING DEVICE

(75) Inventors: Craig R. McCrary, Valencia, CA (US); Thomas R. Thornbury, Los Angeles, CA (US); Arnold M. Heyman, Los Angeles, CA (US)

(73) Assignee: Neotech Products, Inc., Valencia, CA (US)

( * ) Notice: Subject to any disclaimer, the term of this patent is extended or adjusted under 35 U.S.C. 154(b) by 108 days.

(21) Appl. No.: 11/890,161

(22) Filed: Aug. 6, 2007

(65) Prior Publication Data

US 2009/0043286 A1 Feb. 12, 2009

(51) Int. Cl.
*A61M 27/00* (2006.01)
(52) U.S. Cl. .................................................... 604/541
(58) Field of Classification Search ................ 604/118, 604/119, 268, 313, 315, 316, 540, 541, 542, 604/35, 129, 266, 902; 406/152
See application file for complete search history.

(56) References Cited

U.S. PATENT DOCUMENTS

| | | | | | |
|---|---|---|---|---|---|
| 4,729,765 | A | * | 3/1988 | Eckels et al. ................. | 604/540 |
| 4,787,882 | A | * | 11/1988 | Claren ........................ | 604/6.16 |
| 4,790,832 | A | * | 12/1988 | Lopez ......................... | 604/523 |
| 5,676,136 | A | * | 10/1997 | Russo .................... | 128/205.24 |
| 5,730,727 | A | * | 3/1998 | Russo ......................... | 604/118 |
| 5,792,167 | A | * | 8/1998 | Kablik et al. ................ | 606/180 |
| 6,958,050 | B1 | * | 10/2005 | Choski et al. ................. | 604/35 |
| D590,056 | S | * | 4/2009 | McCrary et al. ........... | D24/108 |

* cited by examiner

*Primary Examiner*—Tatyana Zalukaeva
*Assistant Examiner*—Benedict L Hanrahan
(74) *Attorney, Agent, or Firm*—William W. Haefliger

(57) ABSTRACT

A multi-purpose, one integral piece, medical suctioning device, comprising, in combination first, second and third longitudinally extending tubular body portions of successively different outer diameters, and defining a single, molded plastic unit which is laterally flexible along its longitudinal length, the first body portion forming annular barbs outwardly presented to receive connection to plastic tubing, the second body portion defining a cylinder of relatively greater outer diameter or diameters, there being an annular stop ring integral with the cylinder and presented toward such barbs to define a stop surface against which plastic tubing seats endwise, the third body portion being elongated, and tapering away from the second body portion to terminate at a laterally flexible, forward tubular tip, there being a finger controlled air inlet defined by a sideward protrusion integral with said second body portion.

7 Claims, 2 Drawing Sheets

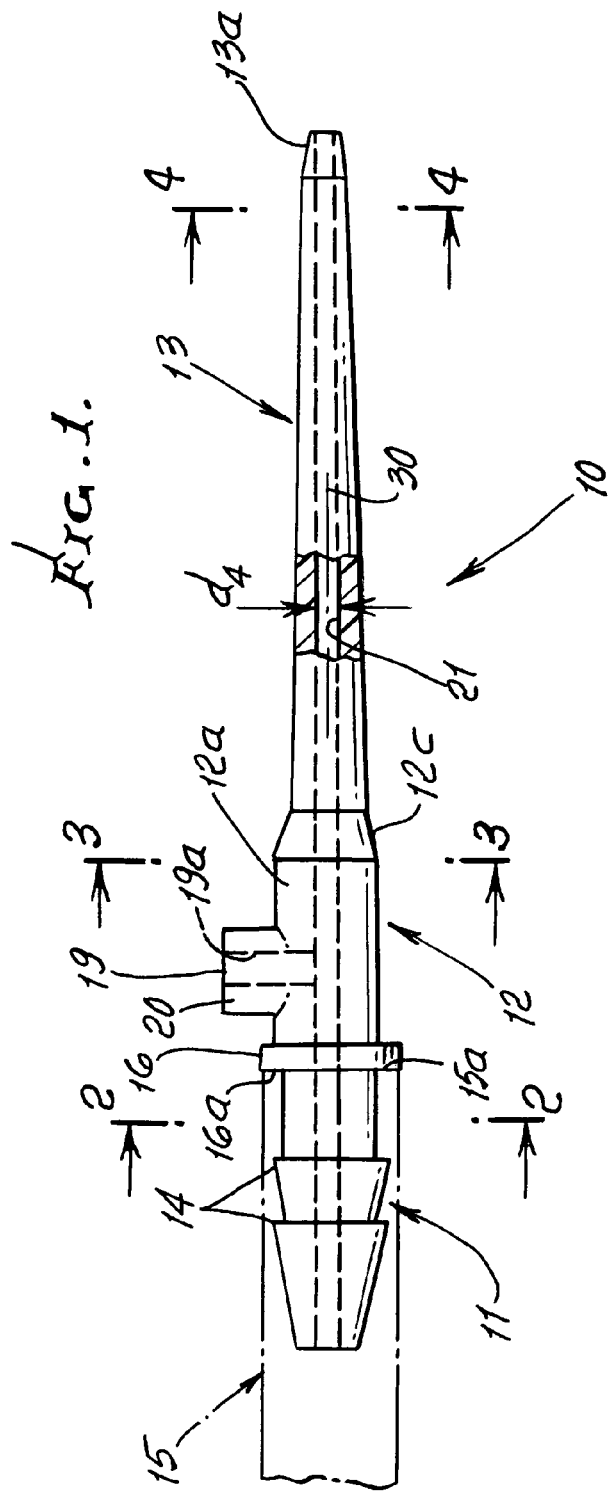
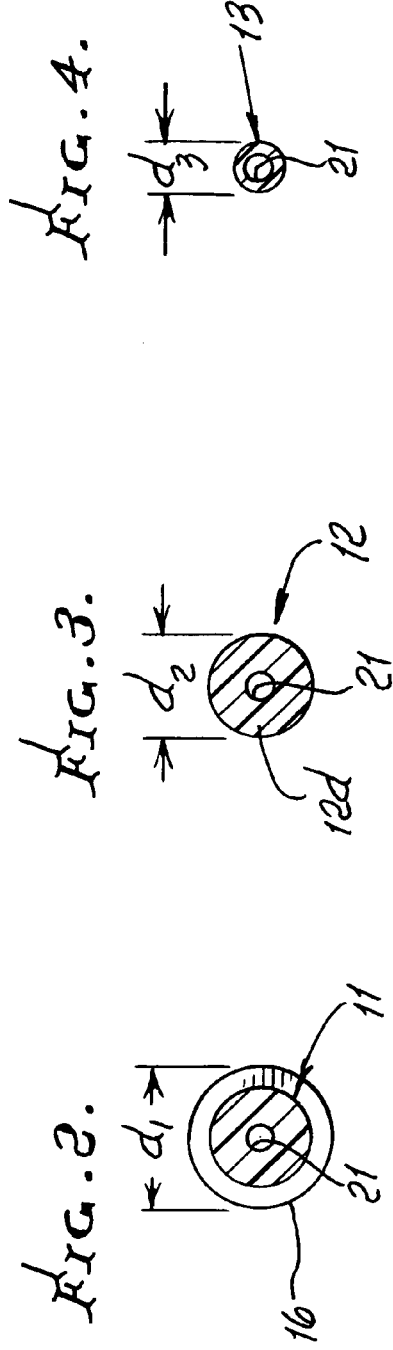

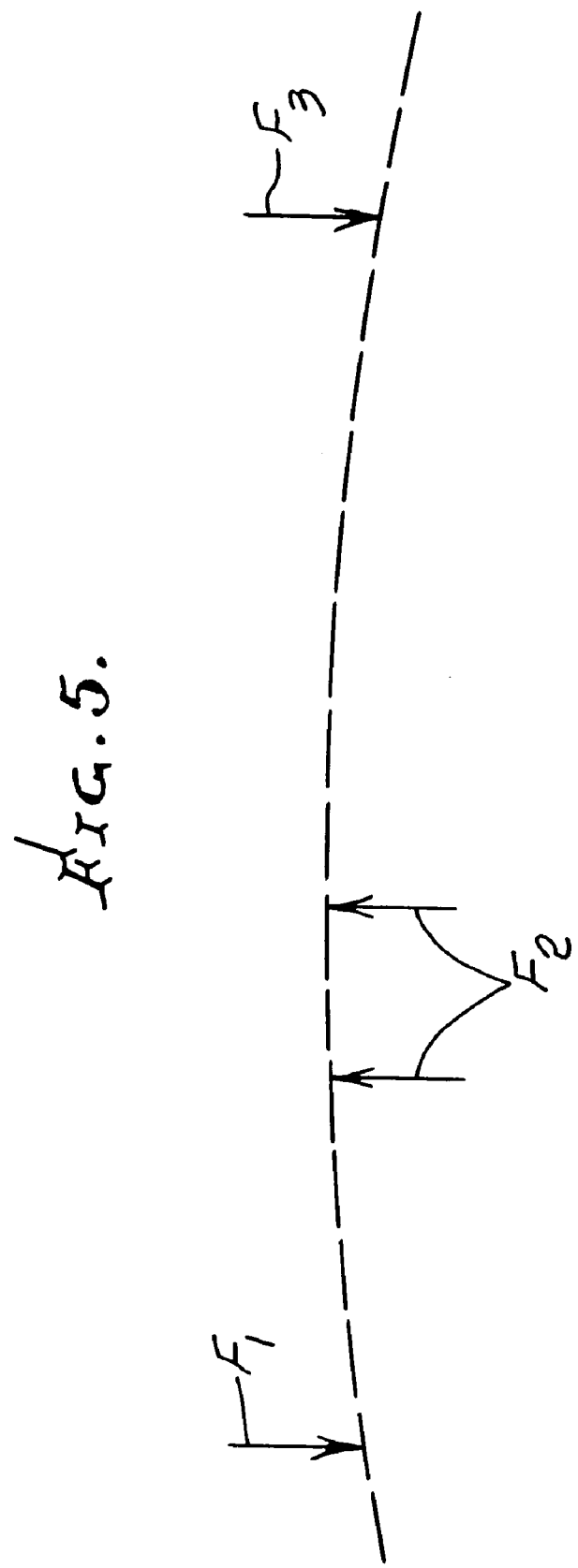

HIGHLY EFFICIENT FLUID SUCTIONING DEVICE

BACKGROUND OF THE INVENTION

This invention relates generally to medical suctioning or aspiration devices and methods, and more particularly to an improved device and method characterized by increased overall utility, as well as ease and effectiveness of use and operation.

There is need for improvements in devices of the type referred to above. Also, there is need for devices and methods embodying the novel and unusual features of construction, modes of operation and results found in the device and methods of use embodied in the present invention.

SUMMARY OF THE INVENTION

It is a major object of the invention to provide an improved suctioning device and method of its use, as referred to. Basically, the device comprises:

a) first, second and third longitudinally extending tubular body portions of successively different outer diameters, and defining a single, molded plastic unit which is laterally flexible along its longitudinal length, b) the first body portion forming annular barbs outwardly presented to receive connection to plastic tubing, c) the second body portion defining a cylinder of relatively greater outer diameter or diameters, there being an annular stop ring integral with the cylinder and presented toward such barbs to define a stop surface against which plastic tubing seats endwise, d) the third body portion being elongated, and tapering away from the second body portion to terminate at a laterally flexible, forwardmost tubular tip, e) there being a finger controlled air inlet defined by a sideward protrusion integral with said second body portion.

A further object is to provide a device as referred to which consists of plastic material which is sidewardly flexible along device length, particularly at the third body portion as referred to, the device thickened at the second body portion to resist flexing. The plastic material of the device may be relatively soft, and sidewardly flexible to greatest extent at said third body portion.

Yet another object is to provide the stop ring to be substantially inflexible sidewardly or radially, the stop ring acting to resist narrowing of a bore formed by the body second tubular portion, for maintaining constant air controlled inlet passage bore diameter at said proximate air inlet, in response to body flexing. That ring typically has outer diameter which exceeds the cylinder outer diameter.

Another object is to provide such a device wherein the cylinder has wall thickness, radially, which substantially exceeds the diameter of the bore within said second body portion.

An additional object includes provision of the first, second and third body portions to consist of translucent plastic material.

A further object is to provide such a device wherein the cylinder has outer diameter along its length which exceeds the outer diameter of said first and third body portions. In this configuration, the stop ring typically has an outer diameter which exceeds the cylinder outer diameter along the cylinder length.

As will be seen, the body portions and stop ring are configured to provide for controlled, differential and relative lateral flexing capabilities of the device body portions, for efficient and comfortable use.

These and other objects and advantages of the invention, as well as the details of an illustrative embodiment, will be more fully understood from the following specification and drawings, in which:

DRAWING DESCRIPTION

FIG. 1 is a side elevation view of a preferred device incorporating the invention;

FIG. 2 is a section taken in elevation on lines 2-2 of FIG. 1, through a flexible tubular first body portion of the FIG. 1 device;

FIG. 3 is a section taken on lines 3-3 of FIG. 1, through a second body portion of the FIG. 1 device;

FIG. 4 is a section taken on lines 4-4 of FIG. 1 through a third elongated portion of FIG. 1; and FIG. 5 is a view showing flexing capability of the FIG. 1 device.

DETAILED DESCRIPTION

The drawings show a preferred multi-purpose, integral medical suctioning device 10 which is of one-piece integrally molded synthetic resinous (plastic) composition and configuration. It includes a) first, second and third longitudinally extending body portions 11-13 of successively different outer diameters, and defining a single, molded plastic unit which is laterally flexible along its length, to readily accommodate to forces applied by a user's hand or fingers, and/or by the infant's body engaged by the device, and/or by other equipment, discomfort to the infant thereby being minimized as during meconium suctioning;

b) the first body portion 11 forming a series of annular barbs 14, radially outwardly presented for receiving connection to plastic tubing, indicated at 15;

c) the second body portion 12 defining a cylinder 12a of relatively greater outer diameter or diameters $d_2$ (than $d_1$), and an annular plastic stop ring 16 integral with cylinder 12a, and presented toward the barbs to define a stop surface 16a against which the end 15a of tubing 15 seats, endwise;

d) the third body portion 13 being elongated lengthwise, and tapering along its length away from the second body part 12, to terminate at laterally flexible tubular tip 13a, tapered as shown;

e) and a finger controllable air inlet 19 at a laterally short sideward protrusion 20 integral with the second body portion 12.

A passage 19a in 20 communicates with an elongated bore 21 of the same diameter $d_4$ extending through 11, 12 and 13. This facilitates one-piece molding of the plastic device, and minimizes frictional resistance to flow of fluid through the device, to tubing 15, as during lateral flexing of the device, enhancing efficiency.

The stop ring 16 is characterized as substantially inflexible sidewardly radially, the stop ring acting to resist narrowing of the bore formed by the body second tubular portion, proximate said air inlet, in response to body flexing. This acts to resist narrowing of the body bore at the second tubular portion 12, proximate the air inlet, as during extreme lateral flexing of the device, enhancing or maintaining air flow efficiency. In this regard, the device typically consists of plastic material which is relatively soft and sidewardly flexible, for example at the third body portion 13. A typical plastic material is DYNAFLEX, a styrene-ethylene/butylene-styrene block copolymer, a product of GLS Corporation, McHenry, Ill., the body portions 11-13 being transparent.

The second body portion 12 is shown to define an outer surface which tapers at 12c between 12a and 13, i.e. toward third body portion 13, which itself tapers along its length toward the tip 13a. In this regard, the cylinder 12 has wall thickness at 12d, radially, and outwardly of bore 21, which substantially exceeds the diameter of the bore within said second body portion. Also, the cylinder 12 has outer diameter $d_3$ along its length, which exceeds the outer diameters of said first and third body portions; and the stop ring outer diameter $d_1$ that substantially exceeds the cylinder outer diameter, and barb outer diameters, enhancing functioning, as by resisting lateral flexing of cylinder 12a and body portion 12 at the air inlet, while allowing lateral flexing of first body portion 11, as seen in FIG. 5.

Finally, the third body portion preferably has reducing wall thickness along its length, and is characterized as allowing relatively extreme sideward flexing of said third body portion along its length in response to sideward force exerted on said third body portion. See FIG. 5.

FIG. 5 also shows the relative lateral flexing capabilities of the body portions 11 and 13 along their length, and relative to the second body portion 12. See the axis 30 of the device and its body portion, flexed in response to forces $F_1$, $F_2$ and $F_3$. Note that the device bore is preferably constant in diameter through the entire device.

The present invention improves on prior U.S. Pat. Nos. 4,729,765 and 6,958,050B1.

We claim:

1. A multi-purpose, integral one-piece, medical suctioning device, comprising, in combination
    a) first, second and third longitudinally extending tubular body portions of successively different outer diameters, and defining a single, molded plastic unit which is laterally flexible along its longitudinal length, each body portion comprising a bore,
    b) said first body portion forming annular barbs outwardly presented to receive connection to plastic tubing,
    c) said second body portion defining an outer diameter greater than the first and third body portion outer diameters, there being an annular stop ring integral with said second body portion and presented toward said barbs to define a stop surface against which said plastic tubing seats endwise,
    d) said third body portion being elongated, and tapering away from said second body portion to terminate at a laterally flexible, forward tubular tip,
    e) there being a finger controlled air inlet defined by a sideward protrusion integral with said second body portion,
    f) said stop ring openly facing said barbs and protrusions and being substantially inflexible sidewardly radially, said stop ring acting to resist narrowing of said bore formed by the second body portion, proximate said air inlet, in response to first and/or third body portion flexing,
    g) said second body portion having wall thickness, radially, which is greater than the diameter of the bore within said second body portion,
    h) and wherein said first, second and third body portions consist of translucent plastic material,
    i) the stop ring openly facing said barbs and said sideward protrusion and being close to said sideward protrusion and acting to resist narrowing of said body bore formed by the second body portion with which the sideward protrusion is integral in response to lateral flexing of the device, said stop ring located between said sideward protrusion and said barbs,
    j) the bores, formed by said first, second and third body portions, extending from an outside end of first body portion to an outside end of third body portion and located radially inwardly of said protrusion, all having the same diameter.

2. The combination of claim 1 wherein said device consists of plastic material which is relatively soft, and sidewardly extremely flexible at said third body portion.

3. The combination of claim 1 wherein said second body portion defines an outer surface which tapers toward and meets said third body portion, to isolate said second body portion from third body portion flexing.

4. The combination of claim 1 wherein the third body portion has relatively reduced wall thickness along its length and characterized as allowing relatively extreme sideward flexing of said third body portion along its length in response to sideward force exerted on said third body portion.

5. The combination of claim 1 wherein said second body portion has outer diameter along its length which exceeds the outer diameters of said first and third body portions.

6. The combination of claim 5 wherein the stop ring has an outer diameter which exceeds the second body portion outer diameter.

7. The method of providing an integral, one-piece medical suctioning device which includes the steps:
    a) providing first, second and third longitudinally extending tubular body portions of successively different outer diameters, and defining a single, molded plastic unit which is laterally flexible along its longitudinal length, each body portion comprising a bore,
    b) said first body portion forming annular barbs outwardly presented to receive connection to plastic tubing,
    c) said second body portion defining an outer diameter greater than the first and third body portion outer diameters there being an annular stop ring integral with said second body portion and presented toward such barbs to define a stop surface against which said plastic tubing seats endwise,
    d) said third body portion being elongated, and tapering away from said second body portion to terminate at a laterally flexible, forward tubular tip,
    e) and providing a finger controlled air inlet defined by a sideward protrusion integral with said second body portion,
    f) said stop ring openly facing said barbs and protrusions and being substantially inflexible sidewardly radially, said stop ring acting to resist narrowing of said bore formed by the second body portion, proximate said air inlet, in response to first and/or third body portion flexing,
    g) said second body portion having wall thickness, radially, which is greater than the diameter of the bore within said second body portion,
    h) and wherein said first, second and third body portions consist of translucent plastic material,
    i) the stop ring openly facing said sideward protrusion and being close to said sideward protrusion and acting to resist narrowing of said body bore formed by the second body portion with which the protrusion is integral, in response to lateral flexing of the device, the stop ring located and projecting between said sideward protrusion and barbs,
    j) the bores, formed by said first, second and third body portions, extending from an outside end of first body portion to an outside end of third body portion and located radially inwardly of said protrusion, all having the same diameter.

* * * * *